United States Patent [19]

Fessner

[11] Patent Number: 5,683,897
[45] Date of Patent: Nov. 4, 1997

[54] ENZYMATIC PROCESS FOR THE PRODUCTION OF DIHYDROXYACETONE PHOSPHATE FROM GLYCEROPHOSPHATE AND ITS USE IN ENZYMATIC ALDOL ADDITIONS

[75] Inventor: Wolf-Dieter Fessner, Gundelfingen, Germany

[73] Assignee: Boehringer Mannheim GmbH, Mannheim, Germany

[21] Appl. No.: 501,114

[22] PCT Filed: Feb. 2, 1994

[86] PCT No.: PCT/EP94/00291

§ 371 Date: Aug. 8, 1995

§ 102(e) Date: Aug. 8, 1995

[87] PCT Pub. No.: WO94/18338

PCT Pub. Date: Aug. 18, 1994

[30] Foreign Application Priority Data

Feb. 11, 1993 [DE] Germany .................. 43 04 097.7

[51] Int. Cl.[6] ............... C12P 9/00; C12P 19/00; C12P 19/02; C12N 9/88
[52] U.S. Cl. ............... 435/105; 435/72; 435/100; 435/177; 435/183; 435/190; 435/232
[58] Field of Search ............... 435/100, 190, 435/105, 232, 72, 183, 177

[56] References Cited

U.S. PATENT DOCUMENTS

| | | | |
|---|---|---|---|
| 4,440,854 | 4/1984 | Whitesides et al. | 435/105 |
| 4,656,133 | 4/1987 | Goux | 435/105 |
| 5,019,505 | 5/1991 | Ferguson et al. | 435/190 |
| 5,143,831 | 9/1992 | Wong et al. | 435/105 |
| 5,162,221 | 11/1992 | Brockamp et al. | 435/232 |
| 5,352,590 | 10/1994 | Kato et al. | 435/105 |

OTHER PUBLICATIONS

Chiu, T–H, et al., "L–Rhamnulose 1–Phosphate Aldolase from *Escherichia coli.* Crystallization and Properties" Biochemistry, pp. 98–108, 1969.

Richards et al. "Preparation and Properties of Yeast Aldolase", Journal of Biological Chemistry, 12: 3177–3184, 1991.

Bednarski et al., "Rabbit Muscle Aldolase as a Catalyst in Organic Synthesis," 111:627–636, 1989.

Abell, et al., "Oxygenase Side Reactions of Acetolactate Synthase and Other Carbanion–Forming Enzymes," Biochemistry, 30: 7883–7887, 1991.

John P. Richard, "Acid–Base Catalysis of the Elimination and isomerization Reactions of Triose Phosphates," J. Am. Chem. Soc. 106, 4926–4936, 1984.

Healy et al., "Reaction of the Carbanionic Aldolase–Substrate Intermediate . . . 1,6–Diphosphate" J. Am. Chem. Soc. 94:22, 7911–7916.

*Primary Examiner*—Herbert J. Lilling
*Attorney, Agent, or Firm*—Felfe & Lynch

[57] ABSTRACT

The invention concerns a process for the production of dihydroxyacetone phosphate (DHAP) by enzymatic oxidation of glycerophosphate in the presence of glycerophosphate oxidase and an $H_2O_2$-decomposing enzyme such as catalase and also concerns the conversion of DHAP formed in situ in a coupled enzymatic aldol addition to produce carbohydrates or corresponding derivatives.

15 Claims, No Drawings

ENZYMATIC PROCESS FOR THE PRODUCTION OF DIHYDROXYACETONE PHOSPHATE FROM GLYCEROPHOSPHATE AND ITS USE IN ENZYMATIC ALDOL ADDITIONS

The invention concerns a process for the production of dihydroxyacetone phosphate (DHAP) by enzymatic oxidation of glycerophosphate as well as its use in situ by conversion in a coupled enzymatic aldol addition.

The stereoselective asymmetric synthesis of polyhydroxylated compounds is of current interest due to their importance as components or precursors of active pharmaceutical substances such as antibiotics or glycosidase inhibitors. Enzymatic aldol additions are a valuable method since these can be used to synthesize all four possible diastereomeric ketoses and certain derivatives under mild reaction conditions in a highly diastereoselective manner and thus in high chemical and optical purity (DE 41 11 971). While the corresponding enzymes, the DHAP aldolases, accept a variety of aldehydes as electrophilic components, these enzymes additionally require dihydroxyacetone phosphate (DHAP) as an essential aldol donor substrate.

Commercial DHAP or direct acetal precursors do not come into consideration as a starting material for technical syntheses for economic reasons. Moreover, free DHAP is relatively unstable and decomposes into methyl glyoxal, which irreversibly inactivates the enzyme and into inorganic phosphate which inhibits aldolases. Although various processes are known for the chemical or enzymatic synthesis of DHAP, each of these has serious disadvantages with regard to complexity and product quality:

The chemical phosphorylation of dihydroxyacetone by phosphoryl chloride in acetonitrile/pyridine yields a product in poor yield (60%, non-reproducible according to several reports) which is highly contaminated with inorganic phosphate (C.-H. Wong and G. M. Whitesides, J. Org. Chem. 1983, 48, 3199).

Dimethoxyacetal, from which DHAP is released by acid hydrolysis, requires a time-consuming synthesis from 3-chloro-1,2-propanediol (8 steps in the synthesis, total yield ca. 17%; C. E. Ballou and H. O. L. Fischer, J. Am. Chem. Soc. 1956, 78, 1659).

The diethylacetal of the dimer can be chemically phosphorylated with a considerable expenditure of material and time (3–5 steps in the synthesis) by three variants e.g. with diphenylchlorophosphate (R. L. Colbran et al., Carbohydr. Res. 1967, 4, 355), phosphoryl chloride (F. Effenberger and Straub, Tetrahedron Lett. 1987, 28, 1641) or dibenzyl-N,N-diethylphosphoramidite (R. L. Pederson et al. Tetrahedron, 1991, 47, 2643). DHAP, which is produced from this precursor by acid hydrolysis, is contaminated with ca. 20% inorganic phosphate and is only obtained in a total yield of 50%.

Enzmatic phosphorylation of dihydroxyacetone by glycerokinase-ATP (D. C. Crans and G. M. Whitesides, J. Am. Chem. Soc. 1985, 107, 7019) yields a DHAP quality which is characterized by a high degree of contamination with acetate and phosphate since the acetyl phosphate used for cofactor regeneration is hydrolytically unstable. The enzyme is irreversibly inactivated to a considerable extent by the strongly electrophilic DHAP and can only be stabilized to a limited extent even by immobilization.

The enzymatic cleavage of fructose-1,6-diphosphate by fructose-1,6-diphosphate-aldolase uses a comparatively elaborate starting material, yields only a low equilibrium concentration of DHAP and is limited to synthetic reactions with the same aldolase (O. Meyerhof and K. Lohmann, Biochem. Z. 1934, 271, 89; W.-D. Fessner and C. Walter, Angew. Chem. 1992, 104, 643).

The enzymatic conversion of glycerol by means of glycerokinase and glycerophosphate oxidase only leads to DHAP in non-isolatable amounts on a nanomolar to micromolar scale (JP 03/228 699, FR 2 620 732, U.S. Pat. No. 4,784,945, DE 3 731 876, EP 0 255 334, EP 0 354 551).

The object of the invention is therefore to produce dihydroxyacetone phosphate in high chemical purity and yield from readily available starting materials and in doing so to work under such mild reaction conditions by means of enzymatic catalysis that the labile product can be converted in situ if possible by all types of DHAP aldolases in a coupled reaction.

The object is achieved by a process for the production of DHAP which is characterized in that glycerol monophosphate is oxidized by glycerophosphate oxidase (GPO) [EC 1.1.3.21] in the presence of oxygen, air or hydrogen peroxide and excess amounts of a $H_2O_2$-decomposing enzyme such as catalase [EC 1.11.1.6]. Depending on the specific enzymatic activity of the enzyme preparation used in each case and due to limitations of enzyme solubility, the enzymes are preferably used in the following concentration ranges: GPO 1–1000 U/ml and catalase 5–1,000,000 U/ml and the catalase activity should be one to one thousand-fold the GPO activity. In the case of soluble enzymes 1–10 U/ml GPO and the 5–100-fold amount of catalase activity is preferably used. Deviations from this may be necessary for particular modifications (e.g. when using enzyme membrane reactors or enzyme immobilisates) which, however, a person skilled in the art can determine by conventional experiments based on the teaching given here. Furthermore it is preferable to work under an oxygen atmosphere and at an increased pressure (1–5 atm). The reaction temperature can be varied between −10° C. and 60° C., preferably between 0° C. and 40° C. and it is quite especially preferred to work at 20° C. to 25° C. if the oxygen solubility is adequate. Alternatively the required oxygen can also be generated by adding an aqueous solution of hydrogen peroxide ($H_2O_2$) as shown in FIG. 1. Surprisingly a DHAP product which is free from other components is obtained by this means.

Higher concentrations of DHAP act as a competitive inhibitor of the glycerophosphate oxidase so that the reaction ends between 60 and 95% conversion, however, as a rule at approximately 90%. This means that the product produced by this process can contain between 40 and 5% glycerophosphate depending on the reaction procedure.

For storage the DHAP can be frozen at −80° C. in the form of the product solution or it can be converted into a form that is stable on storage. Precipitation as the barium salt can for example be used for this (D. C. Crans and G. M. Whitesides, J. Am. Chem. Soc. 1985, 107, 7019) or the solution can be completely concentrated under mild conditions (reduced pressure, cold) upon which the product is obtained as a solid salt. In the latter case the desired salt form of DHAP can be predetermined by selection of the cation (e.g. alkali metal ions) which is introduced with the glycerophosphate.

The process according to the invention for the oxidative production of DHAP can be easily coupled to an enzymatic aldol addition by adding an arbitrary aldehyde (FIG. 1). This finding is also surprising since it would not have been expected that the maximally attained concentration of hydrogen peroxide does not lead to deactivation of DHAP aldolases. Even when using oxygen-saturated solutions and under increased oxygen partial pressure up of to 5 atm overpressure, no adverse influence on enzyme stabilities was found. The possibility of coupling a by-product-free DHAP-producing and a DHAP-consuming reaction not only avoids the product inhibition of glycerophosphate oxidase and thus enables a quantitative conversion of L-glycerol-3-phosphate, but it also almost completely suppresses decomposition of the labile DHAP since this cannot accumulate. Fructose-1,6-diphosphate aldolase [EC 4.1.2.13], tagatose-1,6-diphosphate aldolase [EC 4.1.2.-], fuculose-1-phosphate aldolase [EC 4.1.2.17] or rhamnulose-1-phosphate aldolase [EC 4.1.2.19] come for example into consideration as possible aldolases. The coupled reactions are carried out in an aqueous medium at a weakly acidic pH value (ca. 5.5–8.0, preferably 6.5–7.0). This ensures an adequate stability of the reaction component DHAP and a high enzymatically-catalysed reaction rate.

The aldol adducts are also advantageously obtainable in very high yield and in a pure form as crystalline salts by concentrating the solution, wherein the counter-cation can be selected via the form of the glycerophosphate salt. This aqueous medium can contain up to 50 volume % of an organic cosolvent such as for example lower aliphatic alcohols (methanol, ethanol, n-propanol or i-propanol), dimethylsulfoxide, dimethylformamide or acetonitrile if needed to improve the solubility of lipophilic substrates. However, in this case it must be taken into account that the enzyme activities can be reduced by the presence of organic solvents, it is therefore preferable to use no cosolvent or a maximum of 30 volume % cosolvent.

The process according to the invention can in particular also be used in an advantageous manner for the production of isotope-labelled sugars and their derivatives since the valuable labelled glycerol precursors can be converted in the form of labelled DHAPs or labelled D-glyceraldehyde-3-phosphate that can be produced by isomerization using triosephosphate isomerase [EC 5.3.1.1] into the corresponding aldol products with almost no loss of substance. $^2$H, $^3$H, $^{12}$C, $^{13}$C, $^{17}$O and $^{32}$P come for example into consideration for such a specific labelling.

The use of soluble enzymes facilitates the dosing and determination of residual activities, however, immobilization on solid supports e.g. on Eupergit®C, can also advantageously increase the stability of the enzymes.

Instead of enantiomerically pure L-glycerol-3-phosphate it is also possible within the scope of the process according to the invention to use this substance in the form of mixtures which contain it as a component such as racemic DL-glycerophosphate or mixtures of glycerol-1(2)-monophosphates without incurring a significant loss in reaction rate. This is surprising for a person skilled in the art since enzymes are often inhibited by isomers that are not specific for the corresponding enzyme.

In order to purify the aldol products from the coupled syntheses, the glycerol that results from the non-converted glycerophosphate isomers can be easily separated after the phosphate ester hydrolysis (e.g. by phosphatases) by converting it into the volatile acetone-acetal and heating under a vacuum.

Commercially available glycerophosphate oxidases from various organisms (Boehringer Mannheim GmbH; Sigma Chemie GmbH; specific activity of GPO up to 200 U/mg) are suitable for the process according to the invention. In particular an enzyme preparation from microorganisms (Toyobo) was used within the scope of the present invention.

Aldolases that can be used are likewise either the enzymes sold by the said companies or enzymes isolated by known methods from the bacterial strains stated in DE 41 11 971.

Processes for the production of the starting compounds such as L-glycerol-3-phospate are known. This can for example be achieved by enzymatic phosphorylation of glycerol (D. C. Crans and G. M. Whitesides, J. Am. Chem. Soc. 1985, 107, 7019). Commercial forms of isotope-labelled glycerol can also be phosphorylated using this technique. Other possible starting materials for the process according to the invention such as glycerol monophosphate with various contents of L-enantiomers and in the form of salts formulated in different ways are commercially available.

FIG. 1

Reaction scheme for the enzymatic oxidation of L-glycerol-3-phosphate to DHAP and its use in coupled aldol additions.

The following examples are intended to elucidate the invention in more detail without limiting it.

EXAMPLE 1

Synthesis of dihydroxycetone phosphate

A solution of 17.2 g (100 mmol) L-glycerol-3-phoshoric acid in 500 ml distilled water was adjusted to pH 6.8 with lithium hydroxide and diluted to 1000 ml. Oxygen was passed through until saturation (15 min) and afterwards 1000 U L-glycerol-3-phoshate oxidase (GPO) and 5000 U catalase (specific activity up to 50,000 U/ml; Sigma) were added and the solution was stirred mechanically at 20° C. under an oxygen pressure of ca. 2 atm. The conversion was monitored by an enzymatic assay for DHAP formed as well as by $^1$H and $^{31}$P-NMR spectroscopy. After the reaction was completed (ca. 90% conversion) the solution was filtered over active charcoal, neutralized with 1M lithium hydroxide and rapidly concentrated to dryness at a temperature below 20° C. in a vacuum on a rotary evaporator (cooling trap containing dry ice/acetonitrile). In this process the product precipitated as a colourless, solid Li salt of high purity (ca. 90%; 10% glycerophosphate; <5% inorganic phosphate).

Alternatively L-glycerol-3-phosphate was converted as a potassium or sodium salt in which case the respective DHAP salts were obtained. In these cases the product solutions were adjusted to pH 3-4 with the cation exchanger Dowex® AG50W-X8 (H$^+$-form; Bio-Rad) and frozen at −78° C.

EXAMPLE 2

Synthesis of [2,5-$^{13}$C$_2$]-D-fructose-1,6,-diphosphate

A solution of [2-$^{13}$C]-L-glycerol-3-phosphate (Biscyclohexylammonium salt; 370 mg, 1.0 mmol) in 10 ml water was admixed at pH 6.8 with 50 U GPO, 1000 U catalse, 50 U fructose-1,6-diphosphate aldolase (from E. coli, [EC 4.1.2.13]) and 50 U triose phosphate isomerase ([EC 5.3.1.1]) and stirred mechanically at 25° C. under an oxygen atmosphere until TLC monitoring showed quantitative conversion. After neutralizing with cyclohexylamine, concentrating to ca. 3 ml and diluting with ethanol, pure [2,5-$^{13}$C$_2$]-D-fructose-1,6-disphosphate crystallized as the tetra(cyclohexylammonium) salt. Yield 350 mg (95% of theory).

EXAMPLE 3

Synthesis of D-xylulose-1-phosphate

A solution of L-glycerol-3-phosphate (potassium salt; 1.0 mol) in 10 ml water was admixed at pH 6.8 with 70 U GPO and 1000 U catalase and swirled at 25° C. in an open Erlenmeyer flask at 100 rpm. At ca. 60% conversion according to an enzymatic assay for DHAP, a solution of glycolaldehyde (72 mg, 1.2 mmol) in 1.0 ml water and 50 U fructose-1,6-diphosphate aldolase (from rabbit muscle, [EC 4.1.2.13]) were added and the reaction solution was swirled further. After complete convervion of glycerophosphate or DHAP (monitored by TLC and $^1$H-NMR), the product was isolated by means of ion exchange chromatography on the anion exchanger AG1-X8, (HCO$_3$-form, 4 ml) by elution with triethylammonium hydrogen carbonate. D-Xylulose-1-phosphate was obtained as a colourless solid after conversion into the cyclohexylammonium salt. Chemical yield 410 mg (96% of theory).

EXAMPLE 4

Synthesis of D-ribulose-1-phosphate

A solution of L-glycerol-3-phosphate (Biscyclohexylammonium salt; 370 mg, 1.0 mmol) in 10 ml water saturated with oxygen was admixed at pH 6.8 with 70 U GPO and 1000 U catalase and swirled in a 50 ml hydrogenation flask under positive oxygen pressure at 100 rpm. Similar to example 2 glycolaldehyde and 50 U fuculose-1-phoshate aldolase (from *E. coli* [EC 4.1.2.17]) were added and D-ribulose-1-phosphate was isolated after the reaction was completed as a solid colourless cyclohexylammonium salt. Chemical yield: 396 mg (93% of theory).

EXAMPLE 5

Synthesis of L-fructose-1-phosphate

A solution of L-glycerol-3-phosphate (Biscyclohexylammonium salt; 370 mg, 1.0 mmol) and L-glyceraldehyde (110 mg, 1.2 mmol) in 10 ml water saturated with oxygen was admixed at pH 6.8 with 70 U GPO, 1000 U catalase and 50 U rhamnulose-1-phosphate aldolase (from *E. coli*, [EC 4.1.2.19]) and swirled at 100 rpm until complete conversion under an oxygen atmosphere. After filtration over active charcoal it was adjusted to pH 7.5 with 1.0M ethanolic cyclohexylamine solution and concentrated to dryness on a rotary evaporator. The solid residue was taken up in 0.5 ml water, filtered and admixed with 2.5 ml dry ethanol and with as much dry acetone required to produce a slight turbidity. Crystallization at 4° C. yielded L-fructose-1-phosphate as a cyclohexylammonium salt in the form of colourless needles. Chemical yield 370 mg (85% of theory).

EXAMPLE 6

Synthesis of L-fructose

A solution saturated with oxygen of DL-glycerol-1-phosphate (sodium salt, hexahydrate; 1.62 g, 5.0 mmol) in 25 ml water was admixed with 200 U GPO and 1000 U catalase and mechanically stirred under an oxygen pressure of 2 atm until the reaction solution contained ca. 2 mmol DHAP. Then L-glyceraldehyde (270 mg, 3.0 mmol) and 50 U rhamnulose-1-phosphate aldolase (from *E. coli*, [EC 4.1.2.19]) was added and the reaction solution was stirred until complete conversion. After filtration over active charcoal it was adjusted to pH 5 with an ion exchanger (AG50W-X8, H$^+$ form) and admixed with 100 U acid phosphatase. After complete hydrolysis the phosphate esters (monitored by TLC), the solution was desalted by filtering over 20 ml cation exchanger (AG50W-X8, H$^+$ form) then over 20 ml anion exchanger (AG1-X8, HCO$_3^{31}$ form) and concentrated in a vacuum. In order to separate the glycerol, the residue was taken up in acetone, admixed with a catalytic amount of p-toluene sulfonic acid and after complete conversion, it was freed from solvent and 1,2-isopropylidene glycerol in a high vacuum at ca. 50° C. After taking up the solid residue in water and complete hydrolysis of the sugar acetals, the L-fructose was crystallized from 80% aqueous ethanol. Chemical yield 360 mg (80% of theory).

An analogous experiment starting from a mixture of glycerol-1(2)-monophosphates (sodium salt, pentahydrate, containing ca. 50% DL-1-phosphate and ca. 50% 2-phosphate; 3.06 g, 10 mmol) yielded L-fructose in the same yield after appropriate processing.

I claim:

1. A method for producing dihydroxyacetone phosphate comprising oxidizing at least one member selected from the group consisting of L-glycerol monophosphate and a racemic mixture of DL-glycerol monophosphate with glycerophosphate oxidase in the presence of catalase and a member selected from the group consisting of oxygen, air, and hydrogen peroxide.

2. The method of claim 1, wherein said catalase has an activity level which is one to one thousand fold of the activity level of said glycerophosphate oxidase.

3. The method of claim 1, wherein the concentration of said glycerophosphate oxidase is from 1 to 1000 U/ml and the concentration of said catalase is from 5 to 10$^6$ U/ml.

4. The method of claim 1, wherein said oxidizing is performed under an oxygen atmospheric pressure of about 1–5 atm.

5. The method of claim 1, wherein said oxidizing is performed at a pH of about 5.5–8.0.

6. The method of claim 1, wherein said oxidizing is performed at a temperature of from about 0° to 40° C.

7. The method of claim 1, wherein said oxidizing is performed in the presence of from about 0 to 50% organic solvent.

8. The method of claim 1, wherein said glycerophosphate oxidase is specifically labelled.

9. The method of claim 1, wherein said catalase is in an immobilized form.

10. A method for producing a sugar or sugar derivative from glycerol monophosphate comprising oxidizing glycerol monophosphate with glycerophosphate oxidase in the presence of catalase and a member selected from the group consisting of oxygen, air and hydrogen peroxide, wherein said oxidizing is performed in the presence of an aldolase and an aldehyde.

11. The method of claim 10, wherein said aldolase is selected from the group consisting of fructose-1,6-diphosphate aldolase; tagatose-1,6-diphosphate aldolase; fucolose-1-phosphate aldolase; and rhamulose-1-phoshate aldolase.

12. The method of claim 10, wherein said catalse is in an immobilized form.

13. A method for producing dihydroxyacetone phosphate comprising oxidizing L-glycerol monophosphate with glycerophosphate oxidize in the presence of catalase and a member selected from the group consisting of oxygen, air, and hydrogen peroxide.

14. A method for producing dihydroxyacetone phosphate comprising oxidizing a racemic mixture of DL-glycerol monophosphate with glycerophosphate oxidase, in the presence of catalase and a member selected from the group consisting of oxygen, air, and hydrogen peroxide.

15. A method for producing a sugar or sugar derivative from at least one member selected from the group consisting of L-glycerol monophosphate and a racemic mixture of DL-glycerol monophosphate comprising oxidizing said at least one of said L-glycerol monophosphate and said racemic mixture of DL-glycerol monophosphate with glycerophosphate oxidase in the presence of catalase and a member selected from the group consisting of oxygen, air and hydrogen peroxide, wherein said oxidizing is performed in the presence of an aldolase and an aldehyde.

* * * * *

UNITED STATES PATENT AND TRADEMARK OFFICE
CERTIFICATE OF CORRECTION

PATENT NO. : 5,683,897
DATED : November 4, 1997
INVENTOR(S) : Wolf-Dieter Fessner It is certified that error appears in the above-identified patent and that said Letters Patent is hereby corrected as shown below:

In column 1, line 11, change "asymetric" to -- asymmetric --.
In column 1, line 56, change "Enzmatic" to -- Enzymatic --.
In column 4, line 22, change "dihydroxycetone" to -- dihydroxyacetone --.
In column 4, line 24, change "phoshoric" to -- phosphoric --.
In column 4, line 28, change "phoshate" to -- phosphate --.
In column 4, line 53, change "catalse" to -- catalase --.
In column 5, line 25, change "phoshate" to -- phosphate --.
In column 6, line 1, change "$HCO_3^{31}$" to -- $HCO_3^-$ --.
In Claim 11, column 6, line 52, change "phoshate" to -- phosphate --.
In Claim 12, column 6, line 54, change "catalse" to -- catalase --.
In Claim 13, column 6, line 58, change "oxidize" to -- oxidase --.

Signed and Sealed this

Twenty-second Day of August, 2000

Attest:

Q. TODD DICKINSON

*Attesting Officer*  *Director of Patents and Trademarks*